United States Patent
Hurley et al.

(10) Patent No.: US 7,303,743 B2
(45) Date of Patent: Dec. 4, 2007

(54) ANHYDROUS ANTIPERSPIRANT COMPOSITION

(76) Inventors: Harry J. Hurley, 4119 Echo Valley La., Newtown Square, PA (US) 19073; Walter B. Shelley, 21171 River Rd., Grand Rapids, OH (US) 43522

( * ) Notice: Subject to any disclaimer, the term of this patent is extended or adjusted under 35 U.S.C. 154(b) by 453 days.

(21) Appl. No.: 10/984,496

(22) Filed: Nov. 8, 2004

(65) Prior Publication Data

US 2006/0099163 A1 May 11, 2006

(51) Int. Cl.
*A61Q 15/00* (2006.01)
*A61K 8/00* (2006.01)
*A61K 8/04* (2006.01)

(52) U.S. Cl. .......................... 424/65; 424/68; 424/400; 424/401

(58) Field of Classification Search .................. 424/65, 424/68, 400, 401
See application file for complete search history.

(56) References Cited

U.S. PATENT DOCUMENTS 4,552,753 A  11/1985  Elm et al.

OTHER PUBLICATIONS

Shelley, W.B., Hurley, H.J.: Studies on topical antiperspirant control of axillary hyperhidrosis. Acta Derm Venereol (Stockholm) 55: 241-260, 1975.
Shelley, W.B., Hurley, H.J., Nichols, A.C.: Axillary Odor: Experimental Study of the role of bacteria, apocrien sweat and deodorants. AMA Arch. Dermatol. Syph. 68: 430-436, 1953.
Laden, K., editor; Antiperspirants and Deodorants. 2$^{nd}$ Edition. Revised and Expanded. Marcel Dekker, Inc. New York, 1999. pp. 1-16, 59-214, 233-282, 327-375.
International Search Report for PCT Patent Application No.: PCT/US05/38459, dated Aug. 17, 2007.

*Primary Examiner*—Shelley A. Dodson
(74) *Attorney, Agent, or Firm*—Schnader Harrison Segal & Lewis LLP

(57) ABSTRACT

An anhydrous composition of dry aluminum chloride hexahydrate in Castor Oil CP or in Dehydrated Castor Oil particularly suitable for the treatment of localized hyperhidrosis.

55 Claims, No Drawings

ANHYDROUS ANTIPERSPIRANT COMPOSITION

FIELD OF INVENTION

This invention relates to a composition particularly suitable for treating localized hyperhidrosis.

BACKGROUND OF THE INVENTION

Control of excessive perspiration by use of a topical formulation has long been a medical and social goal. Excessive sweating accounts for intertrigo, infection, dermatitis, and friction blisters of wet soles. It also results in disability for typing and writing due to dripping palms, being handicapped in sporting events from facial sweat, and having a compromised grip on baseball bats, tennis racquets, and basketballs. On the social side, hyperhidrosis induces the embarrassment of wet armpit clothing, gustatory sweating, and auriculotemporal facial sweating (Frey's syndrome), and varied patches of nevoid localized sweating. All intertriginous areas, including fat folds and toe-webs, are susceptible to harm by unevaporated trapped sweat which induces maceration and leads to secondary bacterial and fungal infections. Add to this the cost of dry cleaning clothing and shoe replacement. Total control of sweating by topical means has thus been a long term medical objective.

The first commercial antiperspirant was introduced approximately 100 years ago. It was an aqueous-alcoholic solution of aluminum chloride hexahydrate with an effectiveness now estimated to be 60-70%. Through the century, the effectiveness of commercial antiperspirants has dropped to the 30-55% range due to the industry replacing aluminum chloride hexahydrate with weaker, more alkaline, less irritating salts of aluminum. Indeed, today the FDA approves the label "antiperspirant" for any product that reduces axillary sweating by 20% in 50% of users—and no product can be labeled "stops sweating" (Laden K., Ed., Antiperspirants and Deodorants $2^{nd}$ Edition, 1999).

SUMMARY OF THE INVENTION

The present invention provides a new, super-effective antiperspirant. This has been achieved by using a "hypergolic" reaction pinpointed and limited to the sweat pore. The powerful aluminum chloride hexahydrate is kept inactive in an anhydrous state in castor oil until contact with the microscopic droplets of sweat ignites it, producing poral occlusion.

DESCRIPTION OF INVENTION

Embodiments of the invention address the relative ineffectiveness of currently available commercial antiperspirants by providing an essentially water-free composition of aluminum chloride hexahydrate in a carrier vehicle consisting of either pure castor oil CP (cold press) or pure dehydrated castor oil. This powerful antiperspirant is water activated, and therefore, it is preferable that it not be used on wet skin. Its effectiveness is optimized when activated only by the microscopic sweat droplet coming up from the gland.

By using an absolutely anhydrous system on dry skin, irritation of normal unshaven skin rarely occurs. This unique synergistic system permits use of aluminum chloride hexahydrate in concentrations 8 times the maximum seen in aqueous products and 5 times that in alcoholic products. This invention thereby permits, by varying the concentration of aluminum chloride hexahydrate, a degree of suppression from 20% to virtually 100%.

Control of axillary odor, a serious social menace, is equally impressive since this odor arises as a result of bacterial growth. Use of the compositions provided herein can result in odorless armpits for two weeks after a single application. This is due to the substantivity of these compositions.

Advantageously, the powerful antiperspirant is present in a film that can directly act on the sweat pore. It can be created with no interfering structurants. By eliminating stabilizing and suspending agents, as well as antimicrobials and fragrances, the inventive antiperspirant can be created in a hypo-allergenic form and the maximal focal effect of aluminum chloride hexahydrate can be achieved.

The present invention is designed for the treatment of localized hyperhidrosis. The preferred formulations consist of a single finely ground antiperspirant, i.e. aluminum chloride hexahydrate, in either castor oil CP or dehydrated castor oil, or a mixture of these oils. The aluminum chloride hexahydrate is present in concentrations of from 5.0% to 99.0% based on weight. Illustrative ranges are about 5% to about 60% and about 15% to about 50%. The formulations may be applied with a Roll-On or as a semisolid in a dispenser.

Castor oil CP, also known as ricinus oil, oil of Palma Christi, tangantangan oil, or Neoloid® is a fixed oil obtained by cold pressing the seeds of Ricinus communis. It is a triglyceride of the castor oil fatty acids which are present in a remarkably constant composition, viz.:

| | |
|---|---|
| Ricinoleic Acid | 89.5% |
| Linoleic Acid | 4.2% |
| Oleic Acid | 3.0% |
| Palmitic Acid | 1.0% |
| Stearic Acid | 1.0% |
| Dihydroxystearic Acid | 0.7% |
| Linolenic Acid | 0.3% |
| Eicosanoic Acid | 0.3% |

Castor oil is unique among all fats and oils in that it is the only source of an 18-carbon hydroxylated fatty acid with one double bond, and that approximately 90% of the fatty acid content is ricinoleic acid (12-Hydroxyoleic Acid). It is soluble in alcohol in any proportion and has a viscosity of 7.3 Stokes @ 25° C.

Castor oil is supplied in a variety of grades exhibiting a spectrum of acid values, moisture level, color, and purity (Caschem Inc., Bayonne N.J.). The preferred refined carrier vehicle for this invention is AA® USP (U.S. Pharmacopoeia) because of its anhydrous state and Gardner color value of 2. Other castor oils may be substituted.

The alternative carrier vehicle is dehydrated castor oil. Specifically the preferred oil is Castung® 103G-H (Caschem Inc., Bayonne N.J.). Dehydrated castor oil is manufactured by removing the hydroxyl group and adjacent hydrogen from each ricinoleic acid chain. By creating an addition double bond, two double bonds are present on each chain, of which 25% are in the conjugated position. This oil is a drying linolenic acid free oil in contrast to castor oil which is non-drying. It is odorless, anhydrous, and light colored with an appreciably lower viscosity of 1.8 Stokes @ 25° C.

In the manufacture of these formulations a dry atmosphere is most preferable since aluminum chloride hexahydrate is deliquescent. In an exemplary embodiment of the invention, dry crystals of aluminum chloride hexahydrate USP as supplied, for example, by Spectrum Chemical Manufacturing Corporation New Brunswick, N.J. are fed into a powder processor (Micronizer® Jet Mill, Sturdevant, Hanover, Mass.) in ambient dry air or water free nitrogen gas. The micronized product size is approximately 3 micron to 35 micron, but ideally about 5 micron. This powder is added in a homogenizer to the carrier vehicle, either castor oil CP or dehydrated castor oil (Castung® 103G-H, Caschem Inc., Bayonne N.J.) or a mixture of these two oils. Castung® 103G-H is the preferred vehicle. The substance is then incorporated into an applicator such as a Roll-On unit (for example from Fenton, Weber, and Jones Packaging Inc., Getzville, N.Y.) containing two glass marbles (0.5 inch diameter) or similar solids to promote uniform suspension on shaking. The plastic roller ball is then pressed in place and the cap firmly screwed on. In most embodiments the substance will need to be shaken before using; however, it is possible to add ingredients that would limit separation of the components of the mixture.

The castor oil may be treated to remove unbound water. In an illustrative embodiment, the castor oil is pretreated with molecular sieves, 3A, 8-12 mesh beads to remove unbound water.

Optional Alternatives

Alternatively, the aluminum chloride hexahydrate may be wet-milled in the carrier vehicle to an appropriate fine size, less than about 35 micron, preferably between about 3 microns and 35 microns and most preferably between about 3 and about 6 microns. Milling can be avoided by dissolving the aluminum chloride hexahydrate first in about 0.1% to about 25.0% weight/volume in 200 proof absolute ethyl alcohol.

Preferably nothing is added to the basic composition of aluminum chloride hexahydrate and the castor oil CP or dehydrated castor oil. However, the formulation may if desired contain small amounts of fragrance, e.g. oil of spearmint, dyes, and sensory modifiers, e.g. cyclomethicones. Formulations for aerosols must include propellants well known to the art. Pump sprays are an alternative to the Roll-On applicators and require no additives. Creams and gels may be formulated with emulsifiers and structurants, well known in the art.

Methods of Use

The anhydrous antiperspirant and deodorant compositions of the present invention may be applied topically to the axilla, intertriginous or other areas in an amount completely coating the skin site being treated. The compositions are oily, adherent and substantive.

Preferably, although the compositions can be applied in the A.M. or during the day after drying the skin, they are best applied at bedtime on dry skin. They can be washed or showered off in the morning. The label should read "shake well before use" for compositions of suspended aluminum chloride hexahydrate.

When used on the forehead contact with the eyes or eyelids should be avoided and if applied at night a headband should be worn.

When used on the palms or soles, higher concentrations of the aluminum chloride hexahydrate are necessary and covering the treated palmar or plantar skin with polyvinyldine film (Saran Wrap®) adds to the effectiveness.

The compositions work specifically at the sweat pore when applied to skin that is not wet. These compositions are activated by the sweat droplet in the sweat pore which generates free hydrochloric acid gas at the precise poral site, thereby inducing occlusion at the sweat pore. If the skin is wet the gas covers the entire skin area and hence results in widespread irritation rather than the focal activation precisely at the target sweat pore site. A hair dryer is helpful in drying the skin prior to application of the formulation. The formulations preferably are not used on irritated skin or areas showing shaving cuts or used on sites which have been shaved that day.

| | Formulation Examples | |
|---|---|---|
| 1 | Aluminum chloride hexahydrate (5 micron powder) | 9.0 grams |
| | Dehydrated castor oil (Castung ® 103G-H) | 45 cc |
| 2 | Aluminum chloride hexahydrate | 22.5 cc |
| | 20% solution in water-free ethyl alcohol | |
| | Dehydrated castor oil (Castung ® 103G-H) | 22.5 cc |
| 3 | Aluminum chloride hexahydrate (5 micron powder) | 15 grams |
| | Castor oil USP | 15 cc |

Dispense as semi-solid, preferably in a single sealed packet.

The ratio of aluminum chloride hexahydrate to castor oil is preferably between about 1:1 to 1:5 by weight.

It is noted that although the invention has been described as using castor oil, it is believed that the castor oil ingredient ricinoleic acid can be used instead of castor oil.

While the invention has been described by illustrative embodiments, additional advantages and modifications will occur to those skilled in the art. Therefore, the invention in its broader aspects is not limited to specific details shown and described herein. Modifications, for example, to the relative concentrations and types of components may be made without departing from the spirit and scope of the invention. Accordingly, it is intended that the invention not be limited to the specific illustrative embodiments, but be interpreted within the full spirit and scope of the appended claims and their equivalents.

The invention claimed is:

1. A composition consisting of aluminum chloride hexahydrate incorporated in castor oil.

2. The composition of claim 1 wherein the composition is anhydrous.

3. The composition of claim 1 wherein the castor oil is selected from the group consisting of castor oil CP, dehydrated castor oil and a mixture thereof.

4. The composition of claim 1 wherein the aluminum chloride hexahydrate is present in a range of about 4.0% to about 99.0% by weight.

5. The composition of claim 4 wherein the concentration of the aluminum chloride hexahydrate is present in a range of about 5% to about 60% by weight.

6. The composition of claim 1 wherein the particle size of the aluminum chloride hexahydrate is in the range of about 3 micron to about 35 micron.

7. The composition of claim 6 wherein the particle size of the aluminum chloride hexahydrate is in the range of about 3 micron to about 6 micron.

8. The composition of claim 1 wherein the castor oil is the carrier vehicle.

9. The composition of claim 1 wherein the castor oil is pretreated to remove unbound water.

10. The composition of claim 9 wherein the castor oil is pretreated with molecular sieves, 3A, 8-12 mesh beads to remove unbound water.

11. The composition of claim 1 wherein the aluminum chloride hexahydrate is dissolved in alcohol.

12. The composition of claim 11 wherein the alcohol is anhydrous absolute ethyl alcohol, and the aluminum chloride hexahydrate is in a quantity of from about 0.1% to about 25% by weight/volume.

13. A composition consisting of aluminum chloride hexahydrate incorporated into ricinoleic acid.

14. The composition of claim 13 wherein the composition is anhydrous.

15. The composition of claim 13 wherein the concentration of the aluminum chloride hexahydrate is present in a range of about 4.0% to about 99.0% by weight.

16. The composition of claim 15 wherein the concentration of the aluminum chloride hexahydrate is present in a range of about 5% to about 60% by weight.

17. The composition of claim 13 wherein the particle size of the aluminum chloride hexahydrate is in the range of about 3 micron to about 35 micron.

18. The composition of claim 17 wherein the particle size of the aluminum chloride hexahydrate is in the range of about 3 micron to about 6 micron.

19. The composition of claim 13 wherein the ricinoleic acid is the carrier vehicle.

20. The composition of claim 13 wherein the ricinoleic acid is pretreated to remove unbound water.

21. The method of claim 20 wherein the ricinoleic acid is pretreated with molecular sieves, 3A, 8-12 mesh beads to remove unbound water.

22. The composition of claim 13 wherein the aluminum chloride hexahydrate is dissolved in alcohol.

23. The composition of claim 22 wherein the alcohol is anhydrous absolute ethyl alcohol, and the aluminum chloride hexahydrate is in a quantity of from about 0.1% to about 25% by weight/volume.

24. A method of preparing an antiperspirant comprising:
mixing aluminum chloride hexahydrate with castor oil.

25. The method of claim 24 further comprising:
micronizing the aluminum chloride hexahydrate prior to mixing it with the castor oil.

26. The method of claim 25 further comprising:
micronizing the aluminum chloride hexahydrate after mixing it with the castor oil.

27. The method of claim 24 further comprising pretreating the castor oil to remove unbound water.

28. The method of claim 27 further comprising pretreating the castor oil with molecular sieves, 3A, 8-12 mesh beads to remove unbound water.

29. The method of claim 24 further comprising incorporating the composition into an applicator selected from the group consisting of roll-on, aerosol and pump spray.

30. The method of claim 24 further comprising:
adding emulsifiers, structurants or a combination thereof to the composition to form a cream or gel.

31. The method of claim 24 further comprising:
dissolving the aluminum chloride hexahydrate in alcohol.

32. The method of claim 31 wherein the alcohol is anhydrous absolute ethyl alcohol, and the aluminum chloride hexahydrate is in a quantity of from about 0.1% to about 25% by weight/volume.

33. The method of claim 24 further comprising adding one or more ingredients selected from the group consisting of fragrance, dye, sensory modifier and propellant.

34. The method of claim 24 wherein the concentration of the aluminum chloride hexahydrate is present in a quantity of from 4.0% to 99.0% by weight.

35. The method of claim 34 wherein the concentration of the aluminum chloride hexahydrate is present in a range of about 5% to about 60% by weight.

36. The method of claim 24 further comprising micronizing the aluminum chloride hexahydrate to a particle size of about 3 micron to about 35 micron.

37. The method of claim 36 further comprising micronizing the aluminum chloride hexahydrate to a particle size in the range of about 3 micron to about 6 micron.

38. The method of claim 24 wherein the castor oil is the carrier vehicle.

39. The method of claim 24 further comprising pretreating the castor oil to remove unbound water.

40. The method of claim 39 further comprising pretreating the castor oil with molecular sieves, 3A, 8-12 mesh beads to remove unbound water.

41. A method of preparing an antiperspirant comprising:
mixing aluminum chloride hexahydrate with ricinoleic acid.

42. The method of claim 41 further comprising:
micronizing the aluminum chloride hexahydrate prior to mixing it with the ricinoleic acid.

43. The method of claim 42 further comprising:
micronizing the aluminum chloride hexahydrate after mixing it with the ricinoleic acid.

44. The method of claim 41 further comprising pretreating the ricinoleic acid to remove unbound water.

45. The method of claim 44 further comprising pretreating the ricinoleic acid with molecular sieves, 3A, 8-12 mesh beads to remove unbound water.

46. The method of claim 41 further comprising incorporating the composition into an applicator selected from the group consisting of roll-on, aerosol and pump spray.

47. The method of claim 41 further comprising:
adding emulsifiers, structurants or a combination thereof to the composition to form a cream or gel.

48. The method of claim 41 further comprising:
dissolving the aluminum chloride hexahydrate in alcohol.

49. The method of claim 48 wherein the alcohol is ethyl alcohol.

50. The method of claim 41 further comprising adding one or more ingredients selected from the group consisting of fragrance, dye, sensory modifier and propellant.

51. The method of claim 41 wherein the concentration of the aluminum chloride hexahydrate is present in a quantity of from 4.0% to 99.0% by weight.

52. The method of claim 51 wherein the concentration of the aluminum chloride hexahydrate is present in a quantity of from about 5% to about 60% by weight.

53. The method of claim 41 further comprising micronizing the aluminum chloride hexahydrate to a particle size of about 3 micron to about 35 micron.

54. The method of claim 53 further comprising micronizing the aluminum chloride hexahydrate to a particle size in the range of about 3 micron to about 6 micron.

55. The method of claim 41 wherein the ricinoleic acid is the carrier vehicle.

* * * * *